United States Patent
Chen (10) Patent No.: US 10,117,593 B2
(45) Date of Patent: Nov. 6, 2018

(54) PHYSIOLOGICAL SIGNAL DETECTION CLAMP

(71) Applicant: ZENTAN TECHNOLOGY CO., LTD., New Taipei (TW)

(72) Inventor: Tong-Pie Chen, New Taipei (TW)

(73) Assignee: ZENTAN TECHNOLOGY CO., LTD., New Taipei (TW)

( * ) Notice: Subject to any disclaimer, the term of this patent is extended or adjusted under 35 U.S.C. 154(b) by 0 days.

(21) Appl. No.: 15/228,760

(22) Filed: Aug. 4, 2016

(65) Prior Publication Data

US 2018/0035948 A1 Feb. 8, 2018

(51) Int. Cl.
| A61B 5/0408 | (2006.01) |
| A61B 5/00 | (2006.01) |
| A61B 5/0245 | (2006.01) |
| A61B 5/145 | (2006.01) |
| A61B 5/024 | (2006.01) |

(52) U.S. Cl.
CPC ........ *A61B 5/04085* (2013.01); *A61B 5/0245* (2013.01); *A61B 5/14542* (2013.01); *A61B 5/6838* (2013.01); *A61B 5/02438* (2013.01)

(58) Field of Classification Search
CPC .......................... A61B 5/04085; A61B 5/6838
See application file for complete search history.

(56) References Cited

U.S. PATENT DOCUMENTS

| 4,644,956 | A | * | 2/1987 | Morgenstern | ........ | A61B 5/0416 |
| | | | | | | 600/376 |
| 4,781,197 | A | * | 11/1988 | Fukuda | ................ | A61B 5/0416 |
| | | | | | | 600/384 |
| 5,546,954 | A | * | 8/1996 | Yamada | ............... | A61H 39/002 |
| | | | | | | 600/548 |
| 2009/0062636 | A1 | * | 3/2009 | Muz | ..................... | A61B 5/0416 |
| | | | | | | 600/394 |
| 2012/0272489 | A1 | * | 11/2012 | Wang | .................. | A61B 5/0416 |
| | | | | | | 24/530 |
| 2013/0324827 | A1 | * | 12/2013 | Reitnauer | ............. | A61D 99/00 |
| | | | | | | 600/386 |
| 2016/0128600 | A1 | * | 5/2016 | Su | ........................ | A61B 5/6828 |
| | | | | | | 600/384 |

FOREIGN PATENT DOCUMENTS

DE          19643988          * 4/1998

* cited by examiner

*Primary Examiner* — Lee S Cohen
(74) *Attorney, Agent, or Firm* — Li & Cai Intellectual Property (USA) Office (57) ABSTRACT

A physiological signal detection clamp for being detachably disposed on a fabric worn by a living body, the physiological signal detection clamp includes: a body, two electrode units, a processing unit and a wireless transmission unit. Each of the two opposite side surfaces of the body has a fixing unit. The body is configured to clamp on the fabric by the two fixing unit. When the body is clamped on the fabric, the sensing surfaces of the two electrode units are correspondingly exposed on the outer side surface of the body and attach to the body surface of the living body for detecting the micro electric signal on the body surface of the living body. The processing unit transfers the micro electric signal detected by the electrode unit into a wireless transmission signal, and the wireless transmission unit outputs the wireless transmission signal.

4 Claims, 7 Drawing Sheets

PHYSIOLOGICAL SIGNAL DETECTION CLAMP

BACKGROUND

1. Technical Field

The instant disclosure relates to a physiological signal detection clamp, in particular, to a physiological signal detection clamp which is not secured by tying or secured in a surrounding way.

2. Description of Related Art

Portable physiological signal detection clamps are widely used for detecting physiological signals such as heart beats or blood-oxygen level. Recently, portable physiological signal detection clamps are used by athletes and ordinary persons for monitoring personal health. However, current physiological signal detection clamps are not easy to use. For example, a common heart-beat detection belt is a fabric that surrounds and ties the user's body and hence, is not easy to wear and the user cannot easily move while using it.

SUMMARY

The object of the instant disclosure is to provide a physiological signal detection clamp which is not secured by tying or in a surrounding way.

In order to achieve the object mentioned above, the instant disclosure provides a physiological signal detection clamp for being detachably disposed on a fabric worn by a living body, the physiological signal detection clamp comprises: a body, two electrode units, a processing unit and a wireless transmission unit.

In an embodiment, the body has two opposite side surfaces which are defined as an outer side surface and an inner side surface respectively, and two ends each having a fixing unit, the fixing units correspond to each other; wherein when the body is bent and the two ends thereof are disposed on two opposite sides of the fabric respectively, the fixing units connect with each other and fix the body on the fabric. Two electrode units are fixedly disposed on the body, a sensing surface of each electrode unit is correspondingly exposed on the outer side surface, when the physiological signal detection clamp is fixed on the fabric, the sensing surfaces are correspondingly attached to a body surface of the living body for detecting a micro electric signal on the body surface of the living body. The processing unit is fixedly disposed on the body and electrically connects to the electrode units for transforming the micro electric signal detected by the electrode units into a wireless transmission signal. The wireless transmission unit electrically connects to the processing unit for receiving and transmitting the wireless transmission signal.

In another embodiment, the body is an elastic structure, a bending section is defined at a center position of the body, each of two ends of the bending section has an elastic arm connected thereto, the elastic arms are disposed opposite to each other and are configured to clamp on the fabric; wherein each elastic arm has an inner side surface facing the other elastic arm and a outer side surface opposite to the inner side surface.

In another embodiment, the body is a clamping structure comprising two clamping arms pivotally connected with each other, the two clamping arms are configured to selectively move toward to each other or move away from each other, a side of each clamping arm facing the other clamping arm is defined as an inner side surface and a side opposite to the inner side surface is defined as an outer side surface, each inner side surfaces of the two clamping arms has a fixing unit disposed thereon; when the two clamping arms are disposed on two opposite sides of the fabric respectively, the fixing units connect with each other and fix the clamping structure on the fabric. The two electrode units fixedly disposed on one of the clamping arms, a sensing surface of each electrode unit is correspondingly exposed on the outer side surface of the clamping arm, when the physiological signal detection clamp is fixed on the fabric, the sensing surfaces are attached to a body surface of the living body for detecting a micro electric signal on the body surface of the living body. The processing unit fixedly disposes on the clamping structure and electrically connecting the electrode units for transforming the micro electric signal detected by the electrode units into a wireless transmission signal.

In yet another embodiment, the body comprises two clamping members pivotally connected with each other, each clamping member has an inner side surface facing the other clamping member and an outer side surface opposite to the inner side surface. The recovering unit connects with the two clamping members, when the two clamping members is subjected to stress and move apart from each other, the recovering unit generates a recovering force, and when the two clamping members is no longer subjected to stress, the recovering force drives the two clamping members to move toward each other. The two electrode unit fixedly disposed on one of the clamping member, a sensing surface of each electrode unit is correspondingly exposed on the outer side surface of the clamping arm, when the physiological signal detection clamp is fixed on the fabric, the sensing surfaces are attached to a body surface of the living body for detecting a micro electric signal on the body surface of the living body. The processing unit fixedly disposed on one of the clamping member and electrically connecting the electrode units for transforming the micro electric signal detected by the electrode units into a wireless transmission signal.

The advantages of the instant disclosure are that the user only has to fix the physiological signal detection clamp on the fabric they wear and do not have to surroundingly tie it on the body, thereby increasing the convenience of use.

In order to further understand the techniques, means and effects of the instant disclosure, the following detailed descriptions and appended drawings are hereby referred to, such that, and through which, the purposes, features and aspects of the instant disclosure can be thoroughly and concretely appreciated; however, the appended drawings are merely provided for reference and illustration, without any intention to be used for limiting the instant disclosure.

BRIEF DESCRIPTION OF THE DRAWINGS

The accompanying drawings are included to provide a further understanding of the instant disclosure, and are incorporated in and constitute a part of this specification. The drawings illustrate exemplary embodiments of the instant disclosure and, together with the description, serve to explain the principles of the instant disclosure.

DESCRIPTION OF THE EXEMPLARY EMBODIMENTS

Reference will now be made in detail to the exemplary embodiments of the instant disclosure, examples of which are illustrated in the accompanying drawings. Wherever possible, the same reference numbers are used in the drawings and the description to refer to the same or like parts.

First Embodiment

Figure 1A:
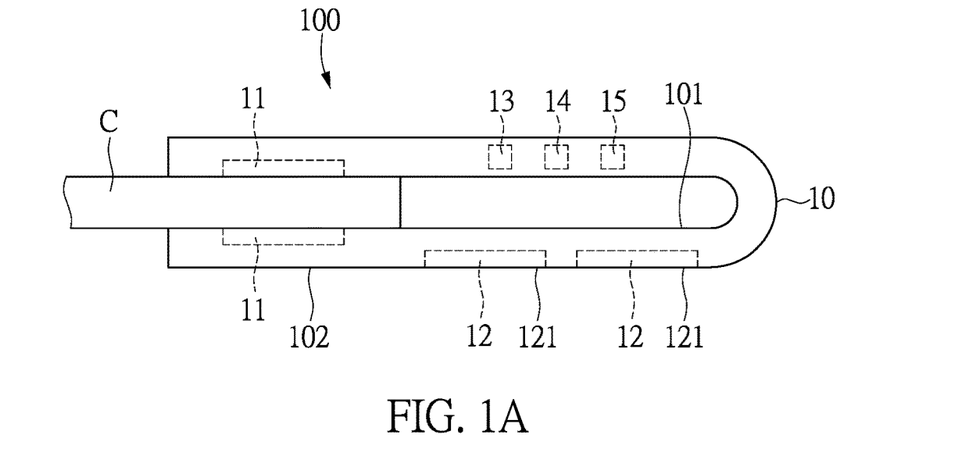
FIGS. 1A and 1B are schematic views of the first embodiment of the physiological signal detection clamp of the instant disclosure.
Figure 1B:
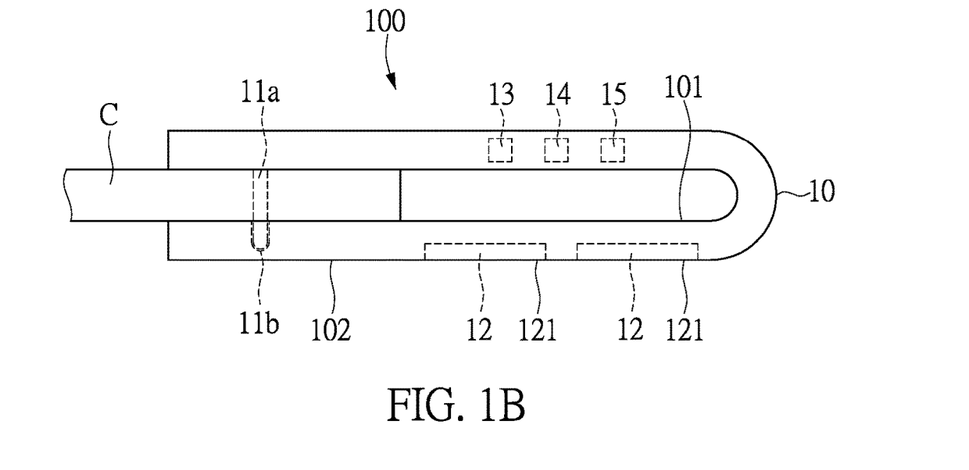

Please refer to FIGS. 1A and 1B. The physiological signal detection clamp 100 comprises a body 10, two fixing units 11, two electrode units 12, a processing unit 13, a wireless transmission unit 14 and a power supply unit 15. The two fixing units 11, the two electrode units 12, the processing unit 13, the wireless transmission unit 14 and the power supply unit 15 are disposed in the body 10.

The two opposite side surfaces of the body 10 are defined as an inner side surface 101 and an outer side surface 102 respectively. Each of the two ends of the body has a fixing unit 11. The center section of the body 10 is configured to bend, and when the center section of the body is bent, the two ends of the body 10 are disposed corresponding to each other, and the fixing units 11 located at the two ends of the body connect with each other. Specifically, the two fixing units 11 can be magnetic elements (such as a permanent magnet) having opposite magnetism, and when the body 10 is bent, the two ends of the body 10 are corresponded to the two opposite sides of the fabric C worn by the living body and hence, the fixing units 11 disposed on the two ends of the body 10 are attracted to each other fixing the body 10 on the fabric C by clamping. The magnetic elements may be an electromagnet in another embodiment.

The two electrode units 12 are spaced from each other and disposed in the body 10. A sensing surface 121 of each electrode unit 12 is correspondingly exposed on the outer surface 102 of the body 10. In actual application, the sensing surfaces 121 of the two electrode units 12 are flush with the outer surface 102 of the body 10. When the body 10 is fixed on the fabric C by the two fixing units 11, the sensing surfaces 121 of the two electrode units 12 attach on the body surface of the living body for detecting the micro electric signal on the body surface of the living body.

Figure 5:
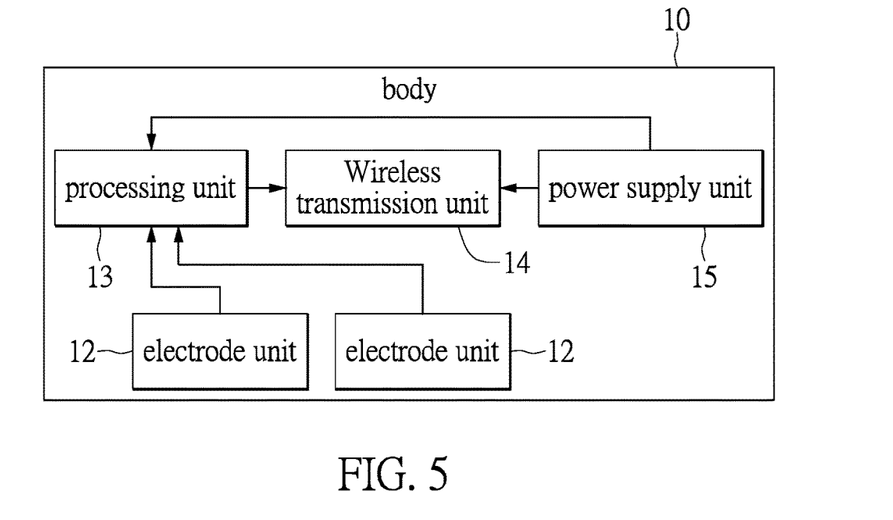
FIG. 5 is a functional block diagram of the first embodiment of the physiological signal detection clamp of the instant disclosure.

The processing unit 13 disposes in the body 10 and electrically connects the two electrode units 12, the wireless transmission unit 14 and the power supply unit 15. The processing unit 13 receives the micro electric signal detected by the two electrode units 12 and transforms the micro electric signal into a wireless transmission signal, then transmits the wireless transmission signal to the wireless transmission unit 14. The processing unit 13 can be a microprocessor. In actual application, the processing unit 13 first resolves the micro electric signal of the two electrode units 12 into specific signals, then transforms the specific signals into a corresponding wireless transmission signal, i.e., after the processing unit 13 transforms the micro electric signal into a corresponding physiological data signal, the processing unit 13 transforms the physiological data signal into a wireless transmission signal. In actual application, the processing unit 13 transforms the micro electric signal at predetermined time intervals.

After the wireless transmission unit 14 receives the wireless transmission signal, the wireless transmission unit 14 transmits the wireless transmission signal to corresponding wireless connecting devices such as personal computers, laptops, smart phones and other related receivers.

The power supply unit 15 can be a detachable battery or an undetachable built-in battery for supplying power to the processing unit 13, the wireless transmission unit 14 and other items needing power and disposed in the body 10.

Please refer to FIG. 1B. In another embodiment, the fixing units 11, which are magnetic elements shown in FIG. 1A, can be a needle-like structure 11a and a buckle structure 11b respectively as shown in FIG. 1B. When the body 10 is bent and the two fixing units 11 are located corresponding to each other, the needle-like structure 11a and the buckle structure 11b can fit with each other, thereby fixing the body 10 on the fabric C. In other words, the two fixing units 11 can be magnetic elements having opposite magnetism or structures that may be fit with each other for steadily fixing the body 10 on the fabric C.

The physiological signal detection clamp 100 can be fixed on the fabric worn by a living body by the two fixing units 11 and attached to the body surface of the living body by the two electrode units 12 for detecting the physiological signals related to the living body. Therefore, the user can quickly and conveniently dispose the physiological signal detection clamp 100. The fabric can be any clothing that is in contact with the living body and the type thereof is not limited herein. Similarly, the living body is not limited to human and can be other animals.

Second Embodiment

Figure 2:
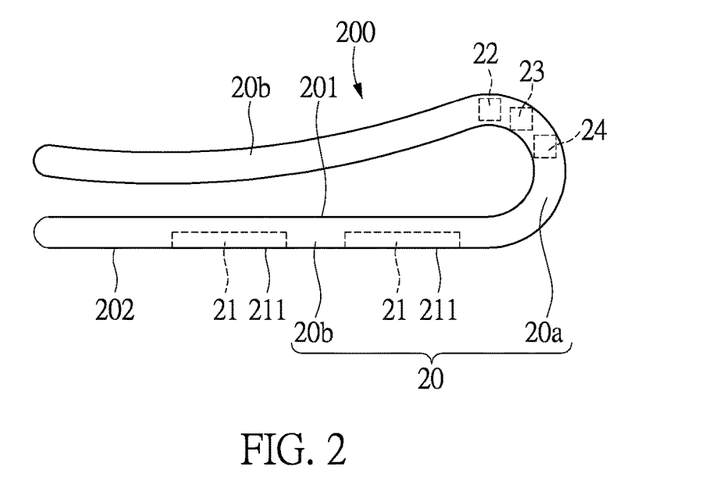
FIG. 2 is a schematic view of the second embodiment of the physiological signal detection clamp of the instant disclosure.

Please refer to FIG. 2, the physiological signal detection clamp 200 comprises a body 20, two electrode units 21, a processing unit 22, a wireless transmission unit 23 and a power supplying unit 24. The two electrode units 21, the processing unit 22, the wireless transmission unit 23 and the power supplying unit 24 are disposed in the body 20.

The body 20 is an elastic structure and has a bending section 20a defined in the center section thereof. The two ends of the bending section 20a connect to an elastic arm 20b respectively, and two elastic arms 20b are disposed corresponding to each other. When the two elastic arms 20b are subjected to an external force and move far away from each other, a recovering force for forcing the two elastic arms 20b to move toward each other is generated by the elastic property and the limitation of the bending section 20a. Therefore, the body 20 is clamped by the two elastic arms 20b on the fabric worn by the living body. Each elastic arm 20b has an inner side surface 201 facing the other elastic arm 20b and an outer side surface 202 opposite to the inner side surface 201. In actual application, the shape of the body 20 and the arrangement of the two elastic arms 20b can be changed as long as the function of clamping can be achieved.

Figure 6:
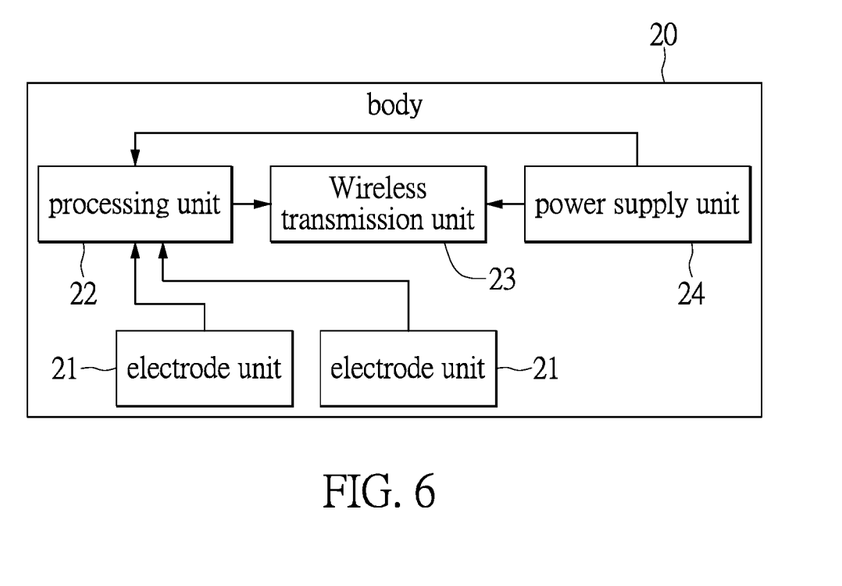
FIG. 6 is a functional block diagram of the second embodiment of the physiological signal detection clamp of the instant disclosure.

The two electrode units 21 are spaced from each other and disposed on one of the elastic arms 20b, and a sensing surface 211 of each electrode unit 21 correspondingly is exposed on the outer side surface 202 of the elastic arm 20b. Therefore, when the two elastic arms 20b clamp on the fabric, the sensing surfaces 211 exposed on the outer side surface 202 of the elastic arm 20b attach to the body surface of the living body for detecting the micro electric signal on the body surface of the living body. The detailed description regarding the processing unit 22, the wireless transmission unit 23 and the power supply unit 24 are described in the previous embodiment, and will not be described herein.

Third Embodiment

Figure 3A:
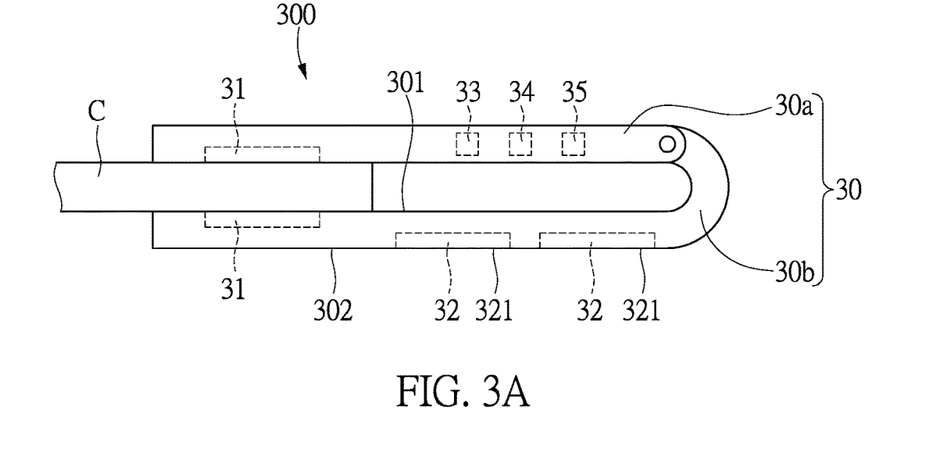
FIGS. 3A and 3B are schematic views of the third embodiment of the physiological signal detection clamp of the instant disclosure.
Figure 3B:
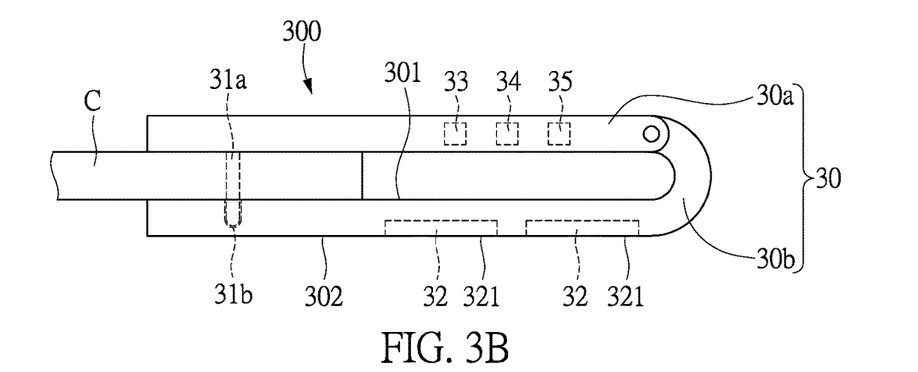
Figure 7:
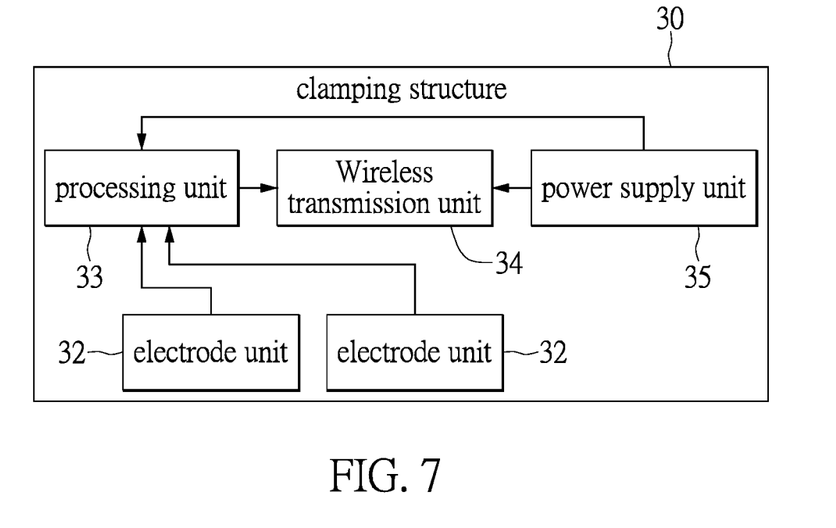
FIG. 7 is a functional block diagram of the third embodiment of the physiological signal detection clamp of the instant disclosure.

Please refer to FIG. 3A and FIG. 3B. The physiological signal detection clamp 300 comprises a clamping structure 30, two fixing units 31, two electrode units 32, a processing unit 33, a wireless transmission unit 34 and a power supply unit 35. The two fixing units 31, the two electrode units 32, the processing unit 33 and the wireless transmission unit 34 are disposed in the clamping structure 30. The detailed description regarding the processing unit 33, the wireless transmission unit 34 and the power supply unit 35 are described in the previous embodiment, and will not be described herein.

The clamping structure 30 comprises two clamping arms 30a, 30b pivotally connected with each other. The two clamping arms 30a, 30b are configured to selectively move toward each other or move away from each other. In actual application, the pivoting manner of the two clamping arms 30a, 30b can be designed based on product requirements, and the shape of the two clamping arms 30a, 30b may vary according to different pivoting manners.

The two clamping arms 30a, 30b each have an inner side surface 301 facing the other clamping arms 30a, 30b, and an outer side surface 302 opposite to the inner side surface 301. The two fixing units 31 correspondingly dispose on the inner surfaces 301 of the two clamping arms 30a, 30b and can be selectively connected to each other. Specifically, as shown in FIG. 3A, the two fixing units 31 can be two magnetic elements having opposite magnetism, and when the two clamping arms 30a, 30b correspondingly dispose on the two opposite side of the fabric C, the two magnetic elements attract to each other and allow the clamping structure 30 to clamp on the fabric C. As shown in FIG. 3B, in another embodiment, the two fixing units 31 can be a needle-like structure 31a and a buckle structure 31b, and the physiological signal detection clamp 300 is fixed on the fabric by fitting and connecting the needle-like structure 31a and the buckle structure 31b of the clamping structure 30 to each other.

The two electrode units are disposed in one of the clamping arms 30b, and a sensing surface of each electrode unit 32 is correspondingly exposed on the outer side surface 302 of the clamping arm 30b. Therefore, when the physiological signal detection clamp 300 is fixed on the fabric C by the clamping structure 30, the sensing surface 321 of each electrode unit 32 attaches on the body surface of the living body to detect the micro electric signal on the body surface of the living body.

Fourth Embodiment

Figure 4:
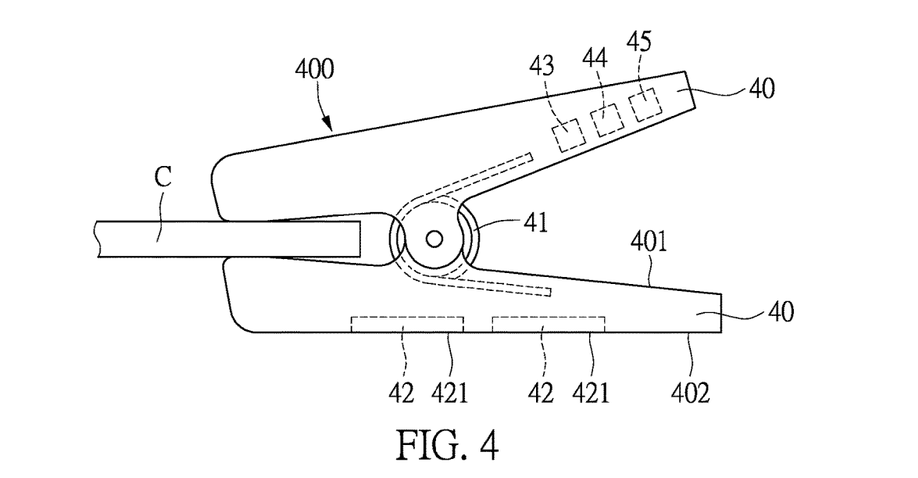
FIG. 4 is a schematic view of the fourth embodiment of the physiological signal detection clamp of the instant disclosure.
Figure 8:
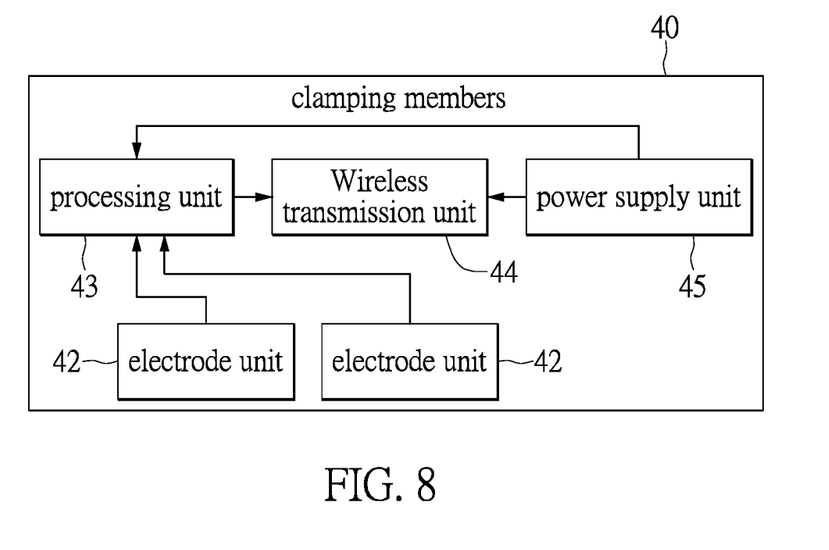
FIG. 8 is a functional block diagram of the fourth embodiment of the physiological signal detection clamp of the instant disclosure.

Please refer to FIG. 4, the physiological signal detection clamp 400 comprises two clamping members 40, a recovering unit 41, two electrode units 42, a processing unit 43, a wireless transmission unit 44 and a power supplying unit 45. The two electrode units 42, the processing unit 43, the wireless transmission unit 44 and the power supply unit 45 are disposed in the two clamping members 40. The detailed description regarding the processing unit 43, the wireless transmission unit 44 and the power supply unit 45 are described in the previous embodiment, and will not be described herein.

The two clamping members 40 pivotally connect to each other, the sides of the two clamping members 30 facing each other are defined as the inner side surfaces 401, and the sides opposite to the inner side surfaces 401 are defined as the outer side surfaces 402. The recovering member 41 connects with the two clamping members 40. When the ends of the clamping members are subjected to a stress and move toward each other, the recovering member 41 correspondingly generates a recovery force, and when the ends of the clamping members 40 are no longer subjected to a stress, the recovery force allows the ends of the clamping members 40 to move away from each other and recover to the original position. Specifically, the recovering member 41 may be a torsional spring and the two clamping members 40 are pivotally connected to each other at substantially the center thereof. The user can press on one end of the two clamping members thereby allowing the other end to clamp on the fabric C worn by the living body.

The two electrode units 42 are disposed in one of the clamping members 40, and a sensing surface 421 of each electrode unit 42 is correspondingly exposed on the outer surface 402 of the clamping member 40. When the two clamping members 40 are correspondingly clamped on the fabric C, the two sensing surfaces 421 attach to the body surface of the living body to detect the micro electric signal on the body surface of the living body. The shape of the outer side surface 402 of the clamping member 40 on which the two electrode units 42 are disposed is preferably a substantially horizontal surface, and the two sensing surfaces 421 are correspondingly flush with the outer side surface 402 for easily attaching the sensing surfaces 421 on the body surface of the living body.

In the above embodiment, the sensing surface 421 of each electrode unit 42 can be a curved surface or another specific shape in certain applications, and is not limited to the flat surface shown in the figure. Similarly, the shape of the electrode units 42 can be designed based on different needs and is not limited to the planar shape as shown in the figures.

The above-mentioned descriptions represent merely the exemplary embodiment of the present disclosure, without any intention to limit the scope of the instant disclosure thereto. Various equivalent changes, alterations or modifications based on the claims of the instant disclosure are all consequently viewed as being embraced by the scope of the instant disclosure.

What is claimed is:

1. A physiological signal detection clamp for being detachably disposed on a fabric worn by a living body, the physiological signal detection clamp comprises:
   a clamping structure comprising two clamping arms pivotally connected with each other, the two clamping arms are configured to selectively close to each other or away from each other, a side of each clamping arm facing the other clamping arm is defined as an inner side surface and a side opposite to the inner side surface is defined as an outer side surface, each inner side surface of the two clamping arms has a fixing unit disposed thereon; when the two clamping arms are disposed on two opposite sides of the fabric respectively, the fixing units connect with each other and fix the clamping structure on the fabric;

two electrode units fixedly disposed on one of the clamping arms, a sensing surface of each electrode unit is correspondingly exposed on the outer side surface of the clamping arm, when the physiological signal detection clamp is fixed on the fabric, the sensing surfaces are correspondingly attached to a body surface of the living body for detecting a micro electric signal on the body surface of the living body;

a processing unit fixedly disposed in the clamping structure and electrically connected to the electrode units for transforming the micro electric signal detected by the electrode units into a wireless transmission signal; and a wireless transmission unit electrically connected to the processing unit for receiving and transmitting the wireless transmission signal.

2. The physiological signal detection clamp according to claim 1, wherein the two fixing units are magnetic elements having opposite magnetism at the side opposite to each other; the physiological signal detection clamp is fixedly disposed on the fabric by the attraction between the two magnetic elements.

3. The physiological signal detection clamp according to claim 1, wherein the fixing units are a needle-like structure and a buckle structure respectively; the needle-like structure and the buckle structure connect with each other for fixedly disposing the physiological signal detection clamp on the fabric.

4. The physiological signal detection clamp according to claim 1, wherein the sensing surface of each electrode unit is flush with the outer side surface corresponding thereto.

* * * * *